United States Patent [19]
Franberg et al.

[11] Patent Number: 5,271,396
[45] Date of Patent: Dec. 21, 1993

[54] ACTIVITY CONTROLLED PACER WITH AUTOMATIC SENSOR RESPONSE AMPLIFICATION ADJUSTMENT

[75] Inventors: Per Franberg, Stockhom; Anders Lindgren, Taeby, both of Sweden

[73] Assignee: Siemens Aktiengesellschaft, Munich, Fed. Rep. of Germany

[21] Appl. No.: 922,395

[22] Filed: Jul. 31, 1992

[30] Foreign Application Priority Data

Aug. 16, 1991 [SE] Sweden ................ 9102376

[51] Int. Cl.⁵ ........................................... A61N 1/365
[52] U.S. Cl. ........................................... 607/17
[58] Field of Search ................ 128/419 PG

[56] References Cited

U.S. PATENT DOCUMENTS

| | | | |
|---|---|---|---|
| 4,428,378 | 1/1984 | Anderson et al. | 128/419 PG |
| 4,856,522 | 8/1989 | Hansen | 128/419 PG |
| 4,870,968 | 10/1989 | Wiertzfeld et al. | 128/419 PG |
| 4,966,146 | 10/1990 | Webb et al. | 128/419 PG |
| 4,972,834 | 11/1990 | Begemann et al. | 128/419 PG |
| 5,016,632 | 5/1991 | Hoegnelid et al. | 128/419 PG |
| 5,031,614 | 7/1991 | Alt | 128/419 PG |
| 5,074,302 | 12/1991 | Poore et al. | 128/419 PG |
| 5,133,349 | 7/1992 | Heinze | 128/419 PG |

FOREIGN PATENT DOCUMENTS

0331309 2/1989 European Pat. Off. ..... 128/419 PG

*Primary Examiner*—William E. Kamm
*Assistant Examiner*—Kennedy J. Schaetzle
*Attorney, Agent, or Firm*—Hill, Steadman & Simpson

[57] ABSTRACT

In an implantable medical device for stimulating a heart, an activity signal from an activity sensor is transformed by response amplification into a stimulation rate at which a stimulation pulse generator delivers stimulating pulses to the heart. The response amplification is automatically optimized because the device contains an evaluation stage which, over a period of time, registers the stimulation rate and then compares this rate to a preset average rate, whereupon a control unit in changes the response amplification so the response amplification is increased when the registered stimulation rate is slower than the average rate and is decreased when the registered stimulation rate is faster than the average rate.

16 Claims, 2 Drawing Sheets

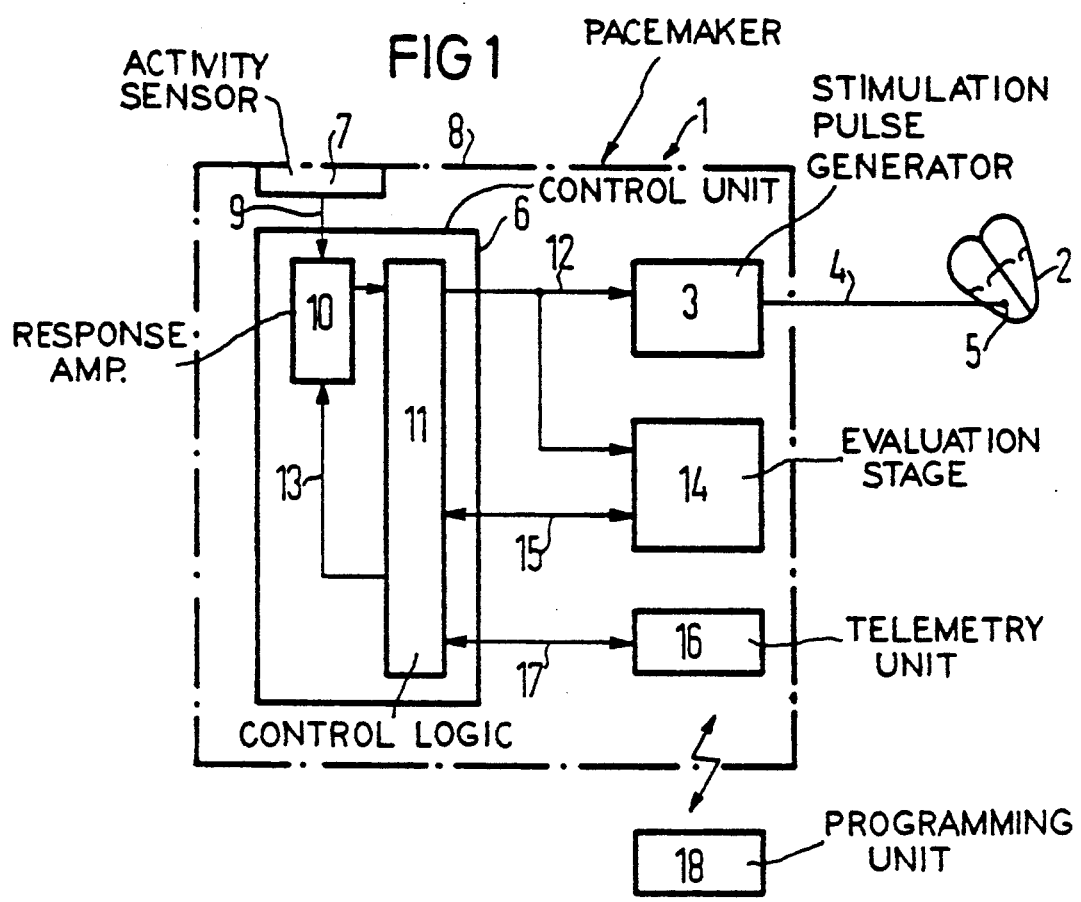
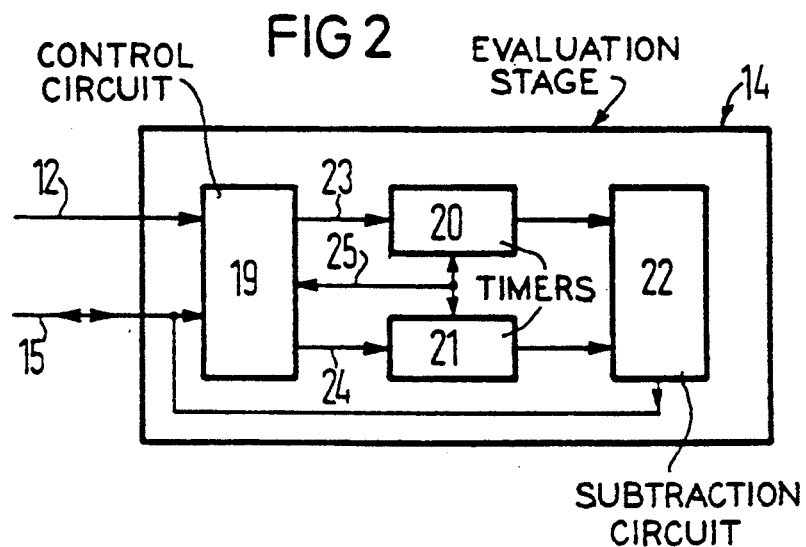

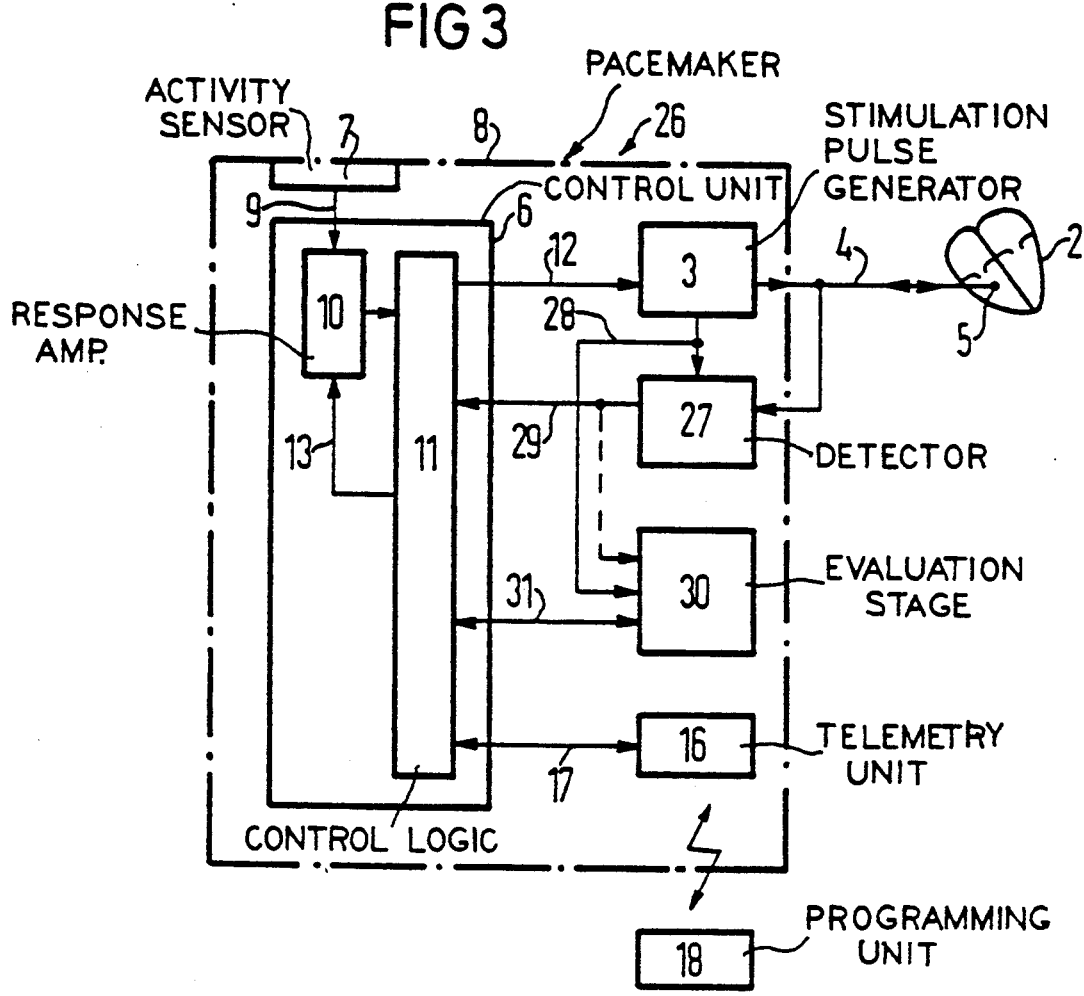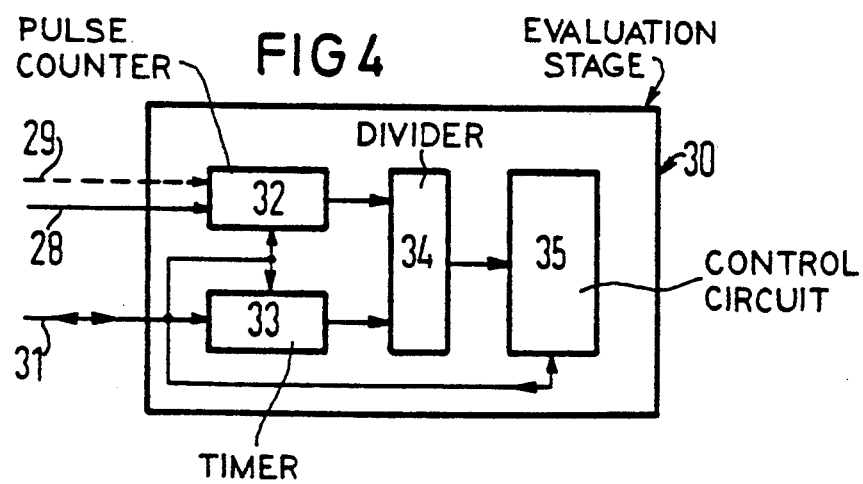

5,271,396

ACTIVITY CONTROLLED PACER WITH AUTOMATIC SENSOR RESPONSE AMPLIFICATION ADJUSTMENT

BACKGROUND OF THE INVENTION

1. Field of the Invention

This invention relates to an implantable medical device for stimulating a heart in vivo of the type including a stimulation pulse generator which generates and delivers stimulating pulses to the heart, an activity sensor which emits an activity signal in response to the living creature's physical activity and a control device which, when the stimulation rate exceeds a preset threshold value, controls the rate at which the stimulation pulse generator delivers stimulating pulses, whereupon every activity signal value is transformed into a stimulation rate signal value by a preset response amplification in the control device.

2. Description of the Prior Art

A prior art example of a related device is disclosed in U.S. Pat. No. 4,428,378 which describes a sensor-controlled pacemaker. An activity sensor transforms sensed mechanical activity into an electric signal which is filtered and amplified by a response amplification so a value is obtained for the stimulation rate at which the heart is to be stimulated. The stimulating pulses are delivered by a stimulation pulse generator which employs the amplified activity signal as an input signal. The response amplification governs the extent to which the stimulation rate is to increase or decrease in response to the pacemaker patient's increased or decreased physical activity. Changes in the stimulation rate are made in the interval between a minimum and a maximum rate, even if the response-amplified signal corresponds to a slower or faster stimulation rate. In this instance, response amplification is linear, and a physician programs the pacemaker with the curve slope he or she feels is suitable for the patient. Prior to this programming, the patient normally performs a brief exercise program to provide the physician with a starting point for the curve slope choice.

Numerous factors, however, can cause the patient's rate during the exercise program to be an inaccurate predictor of the rate the patient will require in daily life. For example, the patient might be ill, or have just recovered from an illness, at the time the response amplification is to be decided. As a result of anxiety, for example, the patient may also be consciously or unconsciously reluctant to perform the exercise program using her/his normal capacity.

Regardless of the reason, the patient's pacemaker may be programmed with response amplification less than ideal for the patient. Depending on the frequency of follow-up appointments, a considerable period of time could elapse before the pacemaker is re-programmed.

SUMMARY OF THE INVENTION

The object of the invention is to provide a medical stimulation device of the type described above in which the response amplification can be automatically optimized for each patient.

This object is achieved in accordance with the principles of the present invention in a medical device of the type described above further having an evaluation stage, which registers the stimulation rate over a period of time and then compares this rate to a preset average rate, and having a pulse control unit, which on the basis of this comparison, then changes the response amplification so it increases when the average stimulation rate registered during the period is slower than the preset average rate and decreases when the registered stimulation rate is faster than the preset average rate.

The preset average rate is a value the physician programs into the device and corresponds to the stimulation rate for an average level of activity by the patient. In optimum circumstances, the average rate would be the rate at which the heart, if healthy, would beat at an average level of patient activity. The device's automatic change in response amplification results in an adaptation of the stimulation rate to the average rate so the average value of the stimulation rate becomes the same as the average rate.

The stimulation rate can be registered continuously or intermittently, i.e., in the form of sampling.

In one embodiment of the stimulation device the evaluation stage has a first timer, which for the aforementioned period of time measures the time during which the stimulation rate is slower than the preset average rate, a second timer, which for the aforementioned period of time measures the time during which the stimulation rate is faster than the preset average rate, and a comparator, which compares the time measured by the first timer to the time measured by the second timer. The response amplification is increased if the time measured by the first timer is longer than the time measured by the second timer, and is decreased if the reverse is the case.

Registration of the stimulation rate occurs in this embodiment by measurement of the time during which the stimulation rate is faster or slower than the average rate and by comparison of the times with one another. The stimulation rate is then balanced around the average rate so it is faster than the average rate for as long as it is slower than the average rate.

In this instance, it is preferable also to change the response amplification on the basis of the magnitude of the difference between the time measured by the first timer and the time measured by the second timer. The response amplification then attains its optimum value more rapidly than if the change were to occur as a sequence of preset adjustment steps.

In an alternative embodiment of the device, the evaluation stage calculates the average value of the registered stimulation rate, and that calculated average value is compared to the preset average value. The control device then changes the response amplification so it increases when the calculated average value is less than the average rate and decreases when the reverse is the case.

The direct link to the average stimulation rate value means that the distribution of stimulation rate values between the minimum and maximum rate is also taken into account in the optimization of response amplification. The average value could, for instance, be calculated by registering the stimulating pulses, measuring registration duration and dividing the number of stimulating pulses by the measured time.

In the same way as in the previous embodiment, the response amplification can be changed based on the magnitude of the difference between the calculated average value of the stimulation rate and the preset average rate.

In both alternatives the stimulation device contains a detector which senses the intrinsic (natural) activity of the heart, and the stimulation device inhibits emission of stimulating pulses when the detector senses intrinsic cardiac activity and suppresses registration of the stimulation rate when the detector detects intrinsic cardiac activity.

Since the device's emitted stimulation rate is used in optimizing the response amplification, it is preferable that intrinsic cardiac activity is filtered out. The amount of existing intrinsic cardiac activity varies widely in different patients as well as in the same patient.

To improve optimization even further and simplify the physician's choice of an appropriate average rate, the aforementioned period of time consists of the aggregate time during which the activity signal exceeds the threshold value. The basic rate which dominates the stimulation rate is therefore filtered out of the evaluation, so only the periods in which the patient is physically active are taken into account. Thus, the patient could, for example, be sick for a time without having any effect on the evaluation.

Alternatively, the stimulation rate could be registered only when the activity signal exceeds the threshold value.

The difference between this alternative and the preceding alternative is that evaluation here takes place over a predetermined real-time period, i.e., a week, on the basis of the activity occurring during this period.

DESCRIPTION OF THE DRAWINGS

FIG. 1 is a schematic block diagram of a first embodiment of a medical stimulation device, in the form of a pacemaker, constructed in accordance with the principles of the present invention.

FIG. 2 is a schematic block diagram of the evaluation stage in the device of FIG. 1.

FIG. 3 is a schematic block diagram of a second embodiment of a medical stimulation device, in the form of a pacemaker, constructed in accordance with the principles of the present invention.

FIG. 4 is a schematic block diagram of the evaluation stage in the device of FIG. 3.

DESCRIPTION OF THE PREFERRED EMBODIMENTS

A pacemaker 1 for stimulation of a heart 2 is shown in FIG. 1. The pacemaker 1 contains a stimulation 15 pulse generator 3, which generates stimulating pulses and delivers them to the heart 2 via an electrode line 4 having an electrode tip 5, and a control unit 6, which via a control line 12 controls the stimulation rate at which the stimulation pulse generator 3 delivers stimulating pulses.

In order to vary the stimulation rate according to a patient's level of physical activity, the pacemaker 1 is equipped with an activity sensor 7. The activity sensor 7 could be i.e., a piezoelectric crystal bonded to the inside of the enclosure 8 of the pacemaker. The enclosure 8 is deflected when the patient moves, and the activity sensor 7 then emits an activity signal which, via a sensor line 9, is transmitted to the control unit 6.

The control unit 6 evaluates and amplifies the activity signal in a response amplifier 10. Physical activity is deemed to exist if the activity signal is greater than a preset threshold value, and the activity signal is transformed by the response amplifier 10 into a stimulation rate signal. The stimulation rate signal is transmitted to control logic 11 in the control device 6 and then, via the control line 12, to the stimulation pulse generator 3. Thus, the response amplifier 10 controls the extent to which the stimulation rate changes for every given change in the activity signal. Variations in the stimulation rate should be made between a minimum and maximum value, i.e., the stimulation rate would then not change further even if the activity signal exceeded an upper threshold value.

Since each patient requires a varying response to changes in her/his level of physical activity due to differences in her/his physical condition etc., the response amplification is variable and is controlled by control logic 11 via a response line 13. For the response amplification to be at a reasonable level for each patient, the pacemaker 1 is equipped with an evaluation stage 14 which compares the stimulation rate during physical activity over a given period of time to a preset average rate corresponding to the patient's heart rate during an average level of physical activity. The evaluation stage 14 is connected to the control line 12 through which signals identifying the current stimulation rate are transmitted and connected to control logic 11 by a duplex information line 15.

A telemetry unit 16 in the pacemaker 1 is connected to control logic 11 by a telemetry line 17 which can exchange information between control logic 11 and the telemetry unit 16. An external programming unit 18 can communicate with the telemetry unit 16. With this unit 18 the physician can program the pacemaker 1 with appropriate parameters, i.e., the average value of the stimulation rate during physical activity. As noted above, the average rate corresponds to the rate at an average level of patient activity. The physician determines an appropriate value for this rate and programs it into the evaluation stage 14 via control logic 11 and the telemetry unit 16.

The operation of the evaluation stage 14 is illustrated in greater detail in FIG. 2. As shown in FIG. 2, the evaluation 14 contains a control circuit 19, a first timer 20, a second timer 21 and a subtraction circuit 22. The first timer 20 is activated by control circuit 19 via a first activating line 23, and the second timer 21 is activated by the control circuit 19 via a second activating line 24. The first timer 20, the second timer 21 and the control circuit 19 are also interconnected by control line 25.

When activity starts, control logic 11 sends a signal through information line 15 to the control circuit 19 in the evaluation device 14. The control circuit 19 then compares the current stimulation rate transmitted on control line 12 with the average rate programmed by the physician with the programming unit 18. If the current stimulation rate is slower than the average rate, the first timer 20 is activated and is maintained active as long as the stimulation rate is slower than the average rate, thereby measuring the time the current stimulation rate is slower than the average rate. If the current stimulation rate is faster that the average rate, the second timer 21 is activated and is maintained active as long as the stimulation rate is faster than the average rate, thereby measuring the time the current stimulation rate is faster than the average rate.

Whenever either of the two timers 20 or 21 reaches a preset time value, it transmits a signal on control line 25 causing the control circuit 19 to instruct the timers 20 and 21 to transfer their respective measurement values to the subtraction circuit 22. The stimulation unit 22 subtracts the measurement value of the first timer 20 from the measurement value of the second timer 21. The difference is sent via information line 15 to control logic 11 in the control unit 6, and the response amplification in the response amplifier 10 is changed via response line 13, depending on the magnitude and sign of the difference. Both timers 20 and 21 are then zeroed, and a new evaluation can commence.

Alternatively, the control circuit 19 could contain a real-time meter and transmission of measurement values from the two timers 20 and 21 would only take place after a preset real-time period, i.e., after a week.

In FIG. 3 there is shown an alternative version of the stimulation device according to the invention in the form of a pacemaker 26. Identical functional elements have the same designation as before. The pacemaker 26 contains an electrode line 4 with an electrode tip 5, a stimulation pulse generator 3, an activity sensor 7, a control unit 6 with a response amplifier 10, control logic 11 and a telemetry unit 16. The pacemaker 26 is also equipped with a detector 27 which senses the heart's 2 intrinsic activity. As long as the heart 2 operates normally, the pacemaker 26 would not need to stimulate. If normal cardiac activity ceases for shorter or longer periods of time, the pacemaker 26 takes over cardiac stimulation. The detector 27 is connected to the heart 2 by the electrode line 4 and electrode tip 5, but could also be connected to the heart 2 by a separate line.

To keep stimulating pulses emitted by the stimulation pulse generator 3 from being detected by the detector 27, the detector 27 is connected to the 25 stimulation pulse generator 3 by a signal line 28. When a stimulation pulse is emitted, the detector 27 is disabled for a specific period of time, i.e., the refractory period. The detector 27 is also connected to the control logic 11 in the control device 6 by a detector line 29. When the detector 27 senses intrinsic cardiac activity, it sends a detection signal to control logic 11 on detector line 29, and control logic 11 then sends a inhibit signal on the control line 12 to the stimulation pulse generator 3, this signal thereby preventing the stimulation pulse generator 3 from sending a stimulation pulse to the heart 2.

In this embodiment, an evaluation stage 30 compares a calculated average value for the stimulation rate when activity is present to the preset average rate. The evaluation stage 30 is therefore connected to the stimulation pulse generator 3 by the signal line 28 5 and to control logic 11 by an information line 31. In order to calculate the prevailing average value, the evaluation stage 30 as shown in FIG. 4, contains a pulse counter 32, a timer 33, a divider 34 and a control circuit 35.

The pulse counter 32 and the timer 33 are activated when activity is present. The pulse counter 32 counts all the stimulating pulses transmitted by the signal line 28, whereas timer 33 measures the time during which stimulating pulses are emitted during ongoing activity. In a manner analogous to the process in the preceding embodiment, measurement can either be performed over a predetermined period of time when activity is present and stimulating pulses are emitted, or over a predetermined real-time period, i.e., a week. When a comparison with the preset average rate is to be made, the control circuit 35 sends a signal via information line 31 to the pulse counter 32 and the timer 33, which transmit the respective measured values to the divider 34. The divider 34 divides the number of measured pulses by the activity duration, thereby providing an average value for the stimulation pulse rate supplied during activity. The calculated average value is sent to the control circuit 35 which compares this average value to the preset average value and transmits the results of the comparison to control logic 11 via information line 31. Control logic 11 then changes the response amplification of the response amplifier 10.

The average value of the sum of the supplied stimulation rate and the detected stimulation rate could also be counted, of course. In this instance, the detector line 29 would also be connected to the pulse counter 32 designated by a dashed line 36 in FIG. 3 and FIG. 4. The pulse counter 32 would count emitted and detected pulses, and the timer 33 measure activity duration as long as any activity continued.

Connection of the detector line 29 to the pulse counter 32 would also offer the physician an opportunity to select an optimum average rate. The intrinsic average pulse rate of the heart would be obtained if the pulse counter 32 were only allowed to count detected pulses and the timer 33 only allowed to measure the time in which detection occurs. A prerequisite for this procedure is that the patient's heart 2 must operate normally at the activity levels occurring at the time and must also operate normally for a sufficiently large part of the time activity occurs. No evaluation of response amplification is possible, however, during this data acquisition. When the pacemaker 26 is to take over cardiac function in such an instance, either prevailing response amplification can be used or the physician can program the pacemaker 26 to stimulate at a fixed basic rate.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable medical device for in vivo stimulation of a heart, said device comprising:
    stimulation pulse generator means for generating and delivering stimulation pulses in vivo to a heart in a patient at a rate;
    means for sensing a parameter indicative of the physical activity level of said patient and for generating an activity signal corresponding to said activity level;
    control means for, when said activity signal exceeds a predetermined threshold, controlling said rate, said control means including means for converting said activity signal into a stimulation rate signal, used to set said rate, by a predetermined response amplification; and
    evaluation means for registering said rate over a period of time to obtain a registered rate and for comparing said registered rate to a predetermined average rate, and for supplying a signal to said control means causing said control means to increase the response amplification if said registered rate is slower than said predetermined average rate and to decrease the response amplification if said registered rate is higher than said predetermined average rate.

2. A device as claimed in claim 1, wherein said evaluation means comprises:
    first timer means for measuring the time during which said rate is slower than said predetermined average rate;

second timer means for measuring the time during which said rate is faster than said predetermined average rate; and comparator means for comparing the time measured by said first timer means to the time measured by said second timer means and for generating said signal supplied to said control means for increasing said response amplification if said time measured by said first timer means is longer than the time measured by said second timer means and for decreasing said response amplification if said time measured by said second timer means is longer than said time measured by said first timer means.

3. A device as claimed in claim 2 further comprising means for measuring the magnitude of the difference between said time measured by said first timer means and said time measured by said second timer means and for changing said response amplification via said signal supplied to said control means based on said magnitude of said difference.

4. A device as claimed in claim 1 wherein said evaluation means comprises:

means for calculating an average value of said registered rate; and means for comparing said average value of said registered rate to said predetermined average value for causing said control means, via said signal supplied to said control means, to increase said response amplification if said calculated average value is less than said predetermined average value and for decreasing the response amplification if said calculated average value is greater than said predetermined average value.

5. A device as claimed in claim 4, wherein said evaluation means further comprises means for determining the magnitude of the difference between said calculated average value and said predetermined average value and for changing said response amplification, via said signal supplied to said control means, based on said magnitude of said difference.

6. A device as claimed in claim 1 further comprising:

detector means for sensing natural cardiac activity and for inhibiting the emission of stimulation pulses by said stimulation pulse generator means if said detector means senses natural cardiac activity and for suppressing registration of said rate when said detector means detects intrinsic cardiac activity.

7. A device as claimed in claim 1 further comprising means for setting said period of time to be an aggregate time during which said activity signal is greater than said threshold value.

8. A device as claimed in claim 1 wherein said evaluation means includes means for limiting the time during which said rate is registered only to that time when said activity signal is greater than said threshold value.

9. A method for operating an implantable medical device for in vivo stimulation of a heart comprising the steps of:

delivering stimulation pulses in vivo to a heart in a patient at a rate;

sensing a parameter indicative of the physiological activity level of said patient and generating an activity signal corresponding to said activity level;

converting said activity signal into a stimulation rate signal, for setting said rate, by a predetermined response amplification;

altering said rate using said stimulation rate signal when said activity signal exceeds a predetermined threshold;

registering said rate over a period of time to obtain a registered rate;

comparing said registered rate to a predetermined average rate; and increasing said response amplification if said registered rate is slower than said predetermined average rate and decreasing said response amplification if said registered rate is higher than said predetermined average rate.

10. A method as claimed in claim 9 wherein the step of registering said rate is further defined by the steps of:

measuring the time during which said rate is slower than said predetermined average rate to obtain a first time;

measuring the time during which said rate is faster than said predetermined average rate to obtain a second time;

comparing said first time to said second time; and wherein the step of increasing said response amplification is further defined by increasing said response amplification if said first time is longer than said second time, and wherein the step of decreasing said response amplification is further defined by decreasing said response amplification if said second time is longer than said first time.

11. A method as claimed in claim 10 comprising the additional steps of:

measuring the magnitude of the difference between said first time and said second time; and additionally changing said response amplification on the basis of said magnitude of said difference.

12. A method as claimed in claim 9 wherein the step of registering said rate is further defined by the steps of:

calculating an average value of said registered rate to obtain a calculated average value;

comparing said calculated average value to said predetermined average value; and wherein the step of increasing said response amplification is further defined by increasing said response amplification if said calculated average value is less than said predetermined average value, and wherein the step of decreasing said response amplification is further defined by decreasing said response amplification if said calculated average value is greater than said predetermined average value.

13. A method as claimed in claim 12 comprising the additional steps of:

determining the magnitude of the difference between said calculated average value and said predetermined average value; and additionally changing said response amplification based on the magnitude of said difference.

14. A method as claimed in claim 9 comprising the additional steps of:

detecting natural cardiac activity of said heart;

inhibiting emission of stimulation pulses when natural cardiac activity is detected; and suppressing registration of said rate when natural cardiac activity is detected.

15. A method as claimed in claim 9 comprising the additional step of setting said period of time at the aggregate time during which said activity is greater than said threshold value.

16. A method as claimed in claim 9 comprising the additional step of:

limiting registration of said rate only to times when said activity signal is greater than said threshold value.

* * * * *